US009562836B2

(12) United States Patent
Gerigk et al.

(10) Patent No.: US 9,562,836 B2
(45) Date of Patent: Feb. 7, 2017

(54) FORMALIN-FREE FIXATION AGENT FOR HISTOLOGICAL STAINS OF TISSUE SAMPLES

(71) Applicant: Roberto Gerigk, Munich (DE)

(72) Inventors: Roberto Gerigk, Muhldorf am Inn (DE); Michael Gudo, Maintal (DE)

(73) Assignee: Roberto Gerigk, Muhldorf am Inn (DE)

( * ) Notice: Subject to any disclaimer, the term of this patent is extended or adjusted under 35 U.S.C. 154(b) by 148 days.

(21) Appl. No.: 14/383,332

(22) PCT Filed: Mar. 1, 2013

(86) PCT No.: PCT/EP2013/054146

§ 371 (c)(1),
(2) Date: Sep. 5, 2014

(87) PCT Pub. No.: WO2013/131816

PCT Pub. Date: Sep. 12, 2013

(65) Prior Publication Data

US 2015/0050689 A1 Feb. 19, 2015

(30) Foreign Application Priority Data

Mar. 6, 2012 (DE) ........................ 10 2012 101 896

(51) Int. Cl.
*G01N 1/36* (2006.01)
*G01N 1/30* (2006.01)

(52) U.S. Cl.
CPC . *G01N 1/36* (2013.01); *G01N 1/30* (2013.01)

(58) Field of Classification Search
CPC ........................................................ G01N 1/36
See application file for complete search history.

(56) References Cited

U.S. PATENT DOCUMENTS

| | | | |
|---|---|---|---|
| 5,196,182 | A | 3/1993 | Ryan |
| 5,849,517 | A | 12/1998 | Ryan |
| 6,072,086 | A | 6/2000 | James et al. |
| 6,319,683 | B1 | 11/2001 | James et al. |
| 2010/0209930 | A1 | 8/2010 | Fernando |

FOREIGN PATENT DOCUMENTS

| | | | | |
|---|---|---|---|---|
| DE | 10-2006-040315 A1 | 3/2008 | | |
| DE | 10-2012-101896.0 | 9/2013 | | |
| EP | 1895287 A3 | 3/2008 | | |
| EP | 1895287 B1 | 12/2009 | | |
| WO | WO-94-04906 A1 | 3/1994 | | |
| WO | WO 9407532 A1 * | 4/1994 | ............. | A61K 39/00 |
| WO | PCT-EP-2013-054146 | 2/2015 | | |

* cited by examiner

*Primary Examiner* — Benjamin Packard
(74) *Attorney, Agent, or Firm* — Douglas Denninger

(57) ABSTRACT

A fixation agent including at least one polyamine and at least one acidification agent. The quality and staining of tissue samples or tissue sections that have not been fixed with formalin is improved, with higher brilliance and color stability of the stain, allowing the tissue to be cut with a better quality without artifacts.

17 Claims, 5 Drawing Sheets

FORMALIN-FREE FIXATION AGENT FOR HISTOLOGICAL STAINS OF TISSUE SAMPLES

This application is a national phase filing under 35 USC §371 of international application No. PCT/EP2013/054146 filed 1 Mar. 2013, which claims priority to German Application No. 10 2012 101 896.0 filed 6 Mar. 2012. The entire contents of each of the above-mentioned applications are incorporated herein by reference.

The invention relates to a development of a fixation solution which effects a clear improvement of the known histological and immunological staining techniques as well as the staining techniques used in pathology. In particular, the present invention improves the quality and staining of tissue samples or tissue sections that have not been fixed with formalin. The present invention has proven to be especially advantageous for sensitive tissue that is difficult to cut when fixed with formalin, which can not only be cut with a better quality without artefacts, but also has a higher brilliance and colour stability of the stain.

FIELD OF THE INVENTION

For histological examinations in biology and medicine, tissue samples are removed, usually fresh, from an organism, or even entire organs or entire animals/animal bodies/plants or organisms, are placed in special solutions known as fixation solutions (infiltration) or are saturated with the fixation solution via a perfusion or instillation arrangement. The fixation serves to fix (=preserve) the state of the tissue at the moment of removal in order to examine this state directly microscopically at a later moment in time and/or to stain it and then microscopically differentiate the stained cell or tissue parts on the basis of their chemical properties and therefore examine these cell or tissue parts or to provide diagnoses.

If a tissue sample is placed in the fixation solution, reference is made to an “immersion fixation”, and if the tissue piece or organ or the entire organism is saturated via its vascular system with the fixation solution, reference is made to perfusion or instillation fixation. The fixation process is a chemical reaction of the actual fixation agent with the proteins of the tissue. A sample is thus preserved, that is to say decomposition processes by enzymes, bacteria or fungi are prevented. In addition, the tissue is hardened and is now converted into a state in which it can be cut using a microtome into thin slices a few μm thick.

Subsequently to the fixation, the tissue sample can be embedded in paraffin, for example. To this end, the sample is usually firstly dewatered in an alcohol series with increasing concentrations. The alcohol is then removed via what is known as an intermedium, the sample is then saturated with paraffin via xylene or a xylene replacement in a number of steps, and lastly is cast in paraffin by means of a mould. Once the paraffin has solidified, the paraffin block thus obtained is processed using a microtome in order to provide thin sections (generally between 2 and 5 μm thick).

A paraffin block can be stored in a practically unlimited manner under room temperature conditions or slightly cooled, that is to say for example individual sections can be produced, and the block can then be stored again and kept for subsequent further processing.

Instead of paraffin, other polymers can also be used for the embedding of samples, for example celloidin, high-molecular PEG, acrylates and others.

Such thin sections are usually arranged on glass slides and then stained in accordance with specific instructions (what are known as histological staining protocols or staining provisions). Only as a result of the staining is it possible to microscopically differentiate differences in the tissue structure, distinguish diseased tissue from healthy tissue, and perform diagnostic assessments, since the stains used bind specifically to certain structures or chemical components of the tissue structures and therefore stain these specifically, that is to say depending on their chemism. For example, cell nuclei can thus be differentiated significantly from cell plasma, and various cell types are stained differently as well as fibres and other tissue components. The overall image of a stain then allows a diagnostic assessment of the examined tissue.

The most conventional fixation agent in histology is formalin. It was used for the first time as fixation agent for tissue samples by Isaak and Ferdinand Blum at the Senckenberg research institute in Frankfurt am Main in the early 1890s and, from the outset, proved to be much better suited, for example compared with spiritus (ethanol), turpentine and other substances (see I. Blum: 1893). Formalin very quickly became widespread in the field of medicine and ultimately established itself globally as the ultimate fixation agent, because it was easy to acquire and easy to handle, and the results are comparable with one another over a broad field of application.

Besides formalin, many further fixation agents were, and are, also used in histology that are based on methanol, ethanol, acetic acid, chloroform, chloral hydrate, picric acid, mercury dichloride, potassium dichromate, chromic acid, osmium tetroxide and various salt solutions and salt mixtures. However, these fixation agents are not all suitable universally, but in each case only specifically for certain tissue types and certain questions and further processing. There is a direct link between fixation (fixation agent), tissue preservation and result of the stain, which ultimately can be evaluated by microscope. Since the fixation in the majority of cases constitutes a chemical reaction (in this respect see “Histological Techniques, Laboratory Columbia Manual University”, 1975), which influences the chemical properties of the tissue, it has long been known already that certain dyes or certain dye solutions are only compatible with certain fixation agents or fixation methods or are incompatible therewith. When, for example, fixation is performed using ethanol or using ethanol/acetic acid mixtures, tissue differentiations can in principle only still be performed with a great deal of difficulty, both because cells and tissue are severely dehydrated in the case of ethanol fixation and shrink, and also because mordant dyes for example do not provide satisfactory results. On the other hand, stains with use for example of picric acid have a much more brilliant and vibrant manifestation than with use of formalin as fixation agent, and therefore pre-treatments of the sections with picric acid are even recommended in some staining protocols.

Although formalin was initially distinguished as an excellent fixation agent, it was observed over time that some problems occurred with numerous staining techniques in histology and pathology. Since formaldehyde oxidises in solution and in contact with the air to form formic acid, what are known as “formalin pigments” form in blood-rich samples. These highly refringent crystals are formed from the reaction of formic acid and blood and are perceived in histology and pathology as interfering artefacts. Stabilisers against the polymerisation, which are added to the commercial formalin solution, such as methanol and butanol, may also negatively influence the results of histological staining, since they act in a dehydrating manner (similarly to ethanol) and interfere with some dye/tissue bonds.

Formalin also plays a central role in a special branch of histology, which is known as immunohistochemistry. Here, however, formalin is not generally used as "formalin 4%", but as "paraformaldehyde solution". Paraformaldehyde (PFA) is the polymerised form of formalin, which is obtainable in the industry as powder and can be dissolved completely in hot, alkaline solution.

Formalin, (the aqueous solution of formaldehyde gas) has the property in aqueous solution of forming chains of paraformaldehyde, which can precipitate. Furthermore, formaldehyde decomposes under the action of light, heat and/or oxygen to form formic acid. In an aqueous formalin solution, degradation and polymerisation reactions take place constantly, as a result of which the formaldehyde is broken down continuously. Since there are also reformation reactions (depolymerisation of the PFA chains, and also balanced reactions), the percentage of formaldehyde in an aqueous solution can never be specified exactly.

The "stock solution", which is known under the trade name "Formol", has a formaldehyde concentration of 35-37%, sometimes also 37-38%. Formol is offered in various qualities: technical, stabilised and buffered. Here, additives are admixed to this saturated formaldehyde solution: stabilised Formol is stabilised with methanol (in order to prevent PFA formation), and buffered Formol is buffered with calcium carbonate, borax or a phosphate mixture (against the reduction of the pH value in the event of decomposition to form formic acid). A 4% formalin solution is then produced from this stock solution by means of dilution (approximately 1+9) and is consequently not exactly 4%, but rather 3.5-3.9%. Some producers offer 4% formalin as "actual" 4% formalin, that is to say the stock solution is not diluted 1+9, but is diluted in accordance with actual percentages by mass.

Nevertheless, the result is also a solution in which the content of formalin fluctuates and reduces successively. For "normal" histological questions, this is largely unproblematic, but for immunohistochemical questions this fluctuating composition, which may additionally have a fluctuating pH value due to the formation of formic acid, may be disadvantageous. Some histological stains are also negatively influenced by an excessively low pH value of formalin (for example the differentiation of oxidative and glycolytic muscle fibres). A fixation solution with exact concentrations of 4%, 6% or 8%, which is adjusted via a buffer to an exact pH value (for example 7.0, 7.2 or 7.4, which corresponds to a conventional pH value of animal/human tissue), is therefore produced from paraformaldehyde for IHC questions. However, such buffered PFA solutions only last for a short period of time, that is to say they have to be used up within a few days, because otherwise exactly the same decomposition and balanced reactions as with normal formalin solution take place. For IHC questions, in which the degree of cross-linking of the proteins with one another plays a key role, buffered PFA is therefore used, because in this case more uniform and more reproducible fixation and reaction conditions are attained.

The disadvantages and inadequacies of formalin (and also of PFA) have long been known and lie not only in their pungent, sharp smell, which is bothersome and unpleasant, but also constitute a significant health risk according to more recent findings. In the EU, a list of the dangerous chemicals (VHCCs or very high concern chemicals) has been compiled and updated within the scope of the REACH Regulation (EC Regulation 1907/2006, with amendments in EC No. 1354/2007 and 1272/2008, implemented in German law in the Chemicals Act of 2 Jul. 2008), and measures have been adopted as to when and how such VHCCs are to be avoided in future or use thereof limited or replaced.

A further disadvantage of formalin-fixed tissue pieces is the fact that such tissue pieces tend to harden over long periods of storage, which has a negative effect on the cuttability and stainability of the tissue. Generally, some tissues that have been fixed in formalin become brittle and cracked and can hardly be cut or can only be cut with difficulty (for example liver, kidneys, spleen, muscles, nerve tissue, brain).

A further negative of formalin is the shrinkage and the dissolving out of fats and glycogen. A shrinkage of up to 10% of the tissue volume is normal in the case of formalin fixations. This leads to cracks in the tissue and also to some sort of misinterpretation in terms of the expansion and size of certain structures.

Considered on the whole, formalin and also buffered PFA in an overall view of the known fixation agents are not the fixation agents that deliver the best results, but rather the fixation agents that deliver comparable results due to the many years of experience and that could be used and acquired cost-effectively.

Another variant of examining tissue in a state that is as fresh as possible is the frozen section. Here, the state is fixed by immediate freezing following the sample removal. Here, however, there is no cross-linking of the proteins with one another. The sample will only last as long as it is held at corresponding low temperature. In addition, the freezing has to be implemented suddenly to very low temperatures (generally <−78° C.), because otherwise the formation of water crystals could destroy fine structures of the tissue. The "frozen section" is what is known as the quick section and is generally produced only for special applications in which, for example, there is no time to wait for the chemical fixation reaction (for example quick diagnostics during an operation) or when the stain or an immunohistochemical detection has been disturbed from the outset by the fixation itself. Under these conditions, a diagnostic decision can be made with the disadvantages of the frozen section.

However, experience generally indicates that stains on fresh tissue are often more intensive and vibrant and that staining times have to be reduced. Where possible, this is due to the fact that the binding of the dyes often is not coupled to the chemical changes caused by the fixation, but because the dyes bind to the tissue components themselves. The chemical fixation reaction can thus be identified here in wide areas as being disruptive for a stain that provides good differentiation.

Consequently, the frozen section would be the qualitatively better approach for many stains if it were not so difficult to handle and to store.

The disadvantages in the case of frozen sections include, for example, the technical outlay of the conservation (immediate freezing following removal), the problem of longer-term storage (the storage temperature may not be exceeded), the relatively thick sections (generally around 10 μm), the impossibility of decalcifying a frozen section, etc. For this reason, the fixation of a tissue sample is a necessary step in order to ensure permanent and longer-term conservation.

For these reasons, there is a considerable need to provide further alternatives that allow comparable or even better stainability of tissue samples and sections, and therefore improve the diagnostic research.

SUMMARY OF THE INVENTION

The provision according to the invention of an alternative fixation agent for tissue samples of all types, in particular for histology and immunohistochemistry, is based precisely on this overall situation and confronts the problem of ensuring that tissue samples of all types, with use of the fixation according to the invention, and also all staining techniques are accessible and enable at least comparable, if not better staining success.

To this end, the invention provides a formalin-free solution, which is suitable for fixing tissue samples of all types and for improving the stainability of the samples. The solution according to the invention is characterised by the fact that, due to the acid present in the composition according to the invention, a total aldehyde concentration of at least 0.5 mol/l, but where necessary also considerably more, can be released.

To this end, the solution according to the invention includes the components of claim 1. Preferred embodiments or applications are formulated in the dependent claims.

In particular, the solution according to the invention contains

- at least one polyamine, selected from the group consisting of urotropine triazines, mono-, di-, tri-, tetra-, penta- or hexamethylol melamine, dimethylol-dihydroxyethylene urea, tetramethylol acetylene diurea, dimethylol propylene urea, acetoguanamine or 5,5-dimethylhydantoin, and mixtures thereof, and
- at least one acidifier selected from the group of free bivalent or polyvalent acids consisting of oxalic acid, fumaric acid, tartaric acid, maleic acid, succinic acid, hydrochloric acid, acetic acid, propionic acid, formic acid, mono-, di- or trichloroacetic acid or chloroacetic acid, boric acid, phosphoric acid, or mixtures thereof, characterised in that the polyamine reacts with the protons released by the acid, thus forming aldehydes. Compositions that for example form formaldehyde, glyoxal, glutaraldehyde, ethanal or propanal and where applicable are able to release these are particularly preferred.

The molar ratio between concentration of the maximum releasable aldehydes in mol to the concentration of the maximum releasable protons in mol is 1:0.7 to 1:1.5, preferably 1:0.7 to 1:0.9, more preferably 1:0.8 to 1:1, more preferably 1:0.9 to 1:1.2, more preferably 1:1 to 1:1.4 and/or more preferably 1:1.2 to 1:1.5 in the solution according to the invention and is therefore selected such that a ratio of at least 0.5 and at most 2 is set between "total releasable aldehyde" and "total protons releasable from the acid".

The solution according to the invention is further characterised in that the solution comprises at least one further polyfunctional aldehyde selected from the group consisting of citral, 3,7-dimethylocta-2,6-dienal, geranial, (E)-3,7-dimethlyocta-2,6-dienal, propanal, butanal, valeric aldehyde, pentanal, hexanal, heptanal, octanal, nonanal, decanal (2 E)-3-phenylprop-2-enal, benzaldehyde, phenylmethanal, vanillin aldehyde, 4-hydroxy-3-methoxyphenylmethanal, and mixtures thereof.

These compounds are preferably aldehydes that still have one or more additional chemical functional groups. These chemical functional groups can be selected from the following: aryl groups, whether phenyl, naphthyl, thienyl, indolyl, etc., linear or branched alkyl, alkenyl or alkyne groups, and also corresponding halogenated groups; groups with oxygen hydroxyl, carbonyl, aldehyde, halogen formyl, carbonate ester, carboxylate, carboxyl, ester, hydroxyperoxy, hydroxy, ether; groups with nitrogen, such as carboxamide, amines, imines, imides, azides, azo, cyanates, nitrates, nitrile, nitrosooxy, nitroso and pyridyl; groups with sulfur such as sulfhydryl, sulfides, disulfides, sulfinyl, sulfonyl, sulfino, sulfates, thiocyanates, carbonothioyl; groups with phosphorous, such as phosphino, phosphono, phosphate.

These groups can occur individually or in multiple, or may also be present in combinations with one another.

Here, the aldehydes for example are present with one or more functions selected from the above-mentioned groups, or what are known as multi-functional aldehydes, because they can bind by means of their aldehyde function to various points of the sample via different chemical mechanisms and provide via their other chemical functions, incorporated and included inherently, docking points for the utilised dyes, which are used in order to stain the sample. Due to the addition of polyfunctional aldehydes, additional chemical functional groups will therefore bind to the tissue sample during the step of tissue fixation.

The chemical functions of the multi-functional aldehydes are selected such that certain types of dyes are bound better than others or are also selected in such a way that certain types of dyes are prevented or discouraged from binding to the sample. Due to the different affinity of the sample, which is also referred to as differentiated chemism of the different tissues, a spatial differentiation of the stainability of the sample is thus attained. The control mechanism thus attained is an advantage of the invention, by means of which the colour contrast of the sample by the addition of multi-functional aldehydes is additionally controlled, because additional docking points and reaction points are provided for the molecules of the dyes due to the binding of these functional groups to the tissue sample, such that an optimal staining can not only be achieved more quickly, but in particular a higher colour intensity, brilliance and/or contrast can also be attained.

In accordance with a further embodiment, a further fixation solution in the context of this invention contains hexamethylol melamine, boric acid, sodium hydroxide, phenylmethanal, Tween 20, wherein hexamethylol melamine is a formaldehyde cleaver, and phenylmethanal serves as polyfunctional aldehyde. The practical implementation for producing this composition will be discussed in the examples.

The molar concentration of the total available aldehyde in the solution according to the invention, which is formed from the polyamine together with the acid, or which is produced by the polyfunctional aldehyde, is preferably set to at least 0.5 mol/l, preferably 0.6-0.69 mol/l, more preferably 0.7-0.79 mol/l, more preferably 0.8-0.89 mol/l, more preferably 0.9-0.99 mol/l, more preferably 0.99-1.2 mol/l, in the solution according to the invention. With such a solution, an optimal fixation of tissue samples is ensured, which improves both the cuttability of the sample and also has a positive influence on the stainability of the sample.

In order to prevent the sample from drying out, a highly hygroscopic chemical can be added to the sample as further additive, which is selected from the group containing monopropylene glycol, dipropylene glycol, polypropylene glycol, glycerol, pentaerythritol, sorbitol, ethylene glycol, diethylene glycol and polyethylene glycol.

In order to reduce the surface tension of the solution and to improve the creep properties, a surfactant can be added to the solution as further additive, which is selected from the group containing ethoxylated non-ionic surfactants with high and/or low HLB value, polysorbates, particularly polysorbate 20, 40, 60 or 80, saponins, alkali salts of decyl sulfates, decyl sulfonates, dodecyl sulfates, dodecyl sulfonates, dodecylbezenesulfonates, oleates, stearates, caprates, caprylates and betaines.

In order to adapt the isotony and osmolarity of the solution, organic or inorganic salts can also be used, which are selected from the group of lithium chlorides, sodium chlorides, potassium chlorides, calcium chlorides, strontium chlorides, lithium sulfates, sodium sulfates, potassium sulfates, calcium sulfates, strontium sulfates, lithium acetates, sodium acetates, potassium acetates, calcium acetates, strontium acetates, lithium citrates, sodium citrates, potassium citrates, calcium citrates, strontium citrates, lithium nitrates, sodium nitrates, potassium nitrates, calcium nitrates, strontium nitrates, lithium succinates, sodium succinates, potassium succinates, calcium succinates, strontium succinates and/or lithium formates, sodium formates, potassium formates, calcium formates, strontium formates.

In order to adapt the flow properties of the solution, organic or inorganic thickening agents can also be used, which are selected from the group of carbomers, starch and modified starch, agarose, dextrose, methyl cellulose, ethyl cellulose or propyl cellulose, acrylic acid and PVA.

In accordance with a further embodiment, the declared solution is present in aqueous form. Furthermore, in accordance with a further embodiment, the components of the declared solution are provided as an anhydrous mixture of crystalline and/or anhydrous components, which are provided in the form of soluble powder or as soluble, pressed tablets. This powder or these tablets is/are dissolved by the addition of water or another suitable solvent or mixture thereof in order to provide a fixation solution that is ready for use.

An advantage of the solution according to the invention is also the pH stability thereof. The solution according to the invention is stable in pH ranges of pH 3-8, preferably pH 3-6. This stability is achieved by the adjustment of the molar ratio of the amine group to the acid groups in a ratio of approximately 1:1. Provided free polyamine is present in the solution, this functions as deposit, and the pH cannot rise. This pH stability is based on the strong buffer capacity of the polyamines, which generally react in a slightly alkaline manner. Due to the reaction of the polyamine, for example urotropine, with the proton of the acid (for example citric acid), an aldehyde and the corresponding ammonium salt are formed. Here, an equilibrium is provided that is influenced by the dissociation constant of the acid and the hydrolysis constant of the polyamine and here adjusts the pH to a certain level-at approximately pH 4 to pH 8. In the case of urotropine, 1 mol of urotropine can consume 6 mol of protons, whereby even small quantities of urotropine or polyamines buffer large quantities of acid, and therefore the pH of the solution is held at a constant value.

Due to this stability, pH fluctuations can be practically excluded. For example a pH change by formation of formic acid is thus also avoided, and therefore it is also impossible to find any "formalin pigments" with use of the solution according to the invention. Additives known to a person skilled in the art for stabilising solutions, which additives could interfere with a stain, such as methanol and butanol, therefore fortunately also are unnecessary.

A further advantage of the solution according to the invention is the colour brilliance and colour intensity of the samples fixed using the solution according to the invention. Thus, practical examples 4-5 for the fixations performed by way of example demonstrate a significant improvement of the morphological preservation and cuttability of the fixed samples. Furthermore, in the case of the performed stains, specifically haematoxylin & eosin, Masson-Goldner Trichrome, MSB-Lendrum and Azan according to Geidies, described in examples 4 and 5, it is shown that a significant improvement of the stainability in general and in particular of the colour saturation and of the colour brilliance is attained by use of the solution according to the invention for fixation. In addition, numerous tissues that are difficult to process, such as brain, skin and testes, can be much better cut and stained with the new fixation.

It is assumed, without introducing a limitation as a result of this assumption, that the improvement of the stainability, even with a small addition of the multi-functional aldehydes, such as citral, 3,7-dimethylocta-2,6-dienal, geranial, (E)-3,7-dimethylocta-2,6-dienal, propanal, butanal, valeric aldehyde, pentanal, hexanal, heptanal, (2 E)-3-phenylprop-2-enal, benzaldehyde, phenylmethanal, vanillin aldehyde, 4-hydroxy-3-methoxyphenylmethanal, heptanal, octanal, nonanal, decanal, and mixtures thereof can be attributed to the fact that they are added together in the balanced reaction.

In the declared solution, such a balanced reaction takes place, in which the polyamine with the protons released by the acid transitions for example into an aldehyde. The added, additional multi-functional aldehydes are summed on the aldehyde side and can then also be incorporated in the sample. The multi-functional groups of these aldehydes serve here as additional docking points for dyes, which can be bound to these points via polar bonds, hydrogen bridges or even covalent bonding, and thus improve the colour reactions of the histological and/or immunohistochemical stains used.

It has fortunately been found that further problems, which are known with other formalin-free fixations, are also evaded or avoided by the use of the declared solution.

Examples include the HOPE fixation (Hepes-Glutamic acid buffer mediated Organic solvent Protection Effect), which is particularly suitable for molecular biological questions, since nucleic acids and antigen structures are preserved particularly well by means of this fixation agent. However, this fixation can be performed only using complex apparatus and by means of a complex processing procedure, and therefore is only suitable with difficulty for daily routine.

Another formalin-free fixation agent is offered by the company Anatech as "prefer fixative". This contains glyoxal, ethanol and buffer; here, however, only few experience values have so far been presented with regard to the histological application. The presence of alcohol in the solution already rules it out, however, for numerous stains.

A further product originates from the company Sigma and is distributed under the name Accustain. Here too, ethanol is the main component of the fixation agent.

Currently, a comprehensive testing and economical evaluation of the results of histological stains is not available for any of the alternative fixation agents. The demands on a formalin-free fixation agent are primarily a comparability of the result with previous results of formalin-fixed samples, and identical or improved handling as a matter of routine, identical or similar fixation periods, and identical or improved staining properties.

The solution according to the invention meets these demands and for the first time allows the fixation and staining of tissue samples fixed in a formalin-free manner whilst maintaining and even considerably improving the colour saturation, colour brilliance and colour intensity in the methods listed hereinafter:

a) Haematoxylin & Eosin staining, with use of various haematoxylin solutions (according to Mayer, Gill, Harris, Weigert, Verhoff, Hansen, etc.) and Eosin solutions (in aqueous, alcohol or methanol form with various concentrations and additives of acetic acid or other pH-lowering additives).
b) Trichrome staining, for example according to Masson, Masson-Goldner, Azan, Crossmon, Mallory, Cason, and other staining protocols which attain a single-, two-, three- or multi-stage stain via nuclear stains, plasma stains and fibre stains.
c) Tri-, tetra-, penta- and poly-chromatic overview and special stains, such as Movat pentachrome, Mollier quadruple staining, van Gieson, Hansen, Weigert and other stains for the physiological or chemical staining of special tissue structures.
d) Special stains or special detections of fibres, tissue components, cell nuclei, plasma components and chemical properties, such as elastica stains, aldehyde detections, iron detections, other metal detections, amyloid detections, fat staining, representation of mucopolysaccharides, silver stains and gold toning, selective nucleus stains, cytological and haematological stains, calcium detections, bone and cartilage stains, nerve stains, etc.

For all mentioned staining methods, it should be ensured that, subsequent to the fixation, the tissue pieces placed in the fixation agent or tissue pieces, organs or entire organisms saturated with the fixation agent are subjected to a conventional further processing that is routine in the laboratory, that is to say they are dewatered and then infiltrated with paraffin or other embedding media (celloidin, acrylates) and processed to form sample blocks, which can ultimately be cut using a microtome.

Here, the invention improves the plastic properties of the fixed material, such that, when processing thin sections, cutting artefacts are absent or only occur to a small extent, because on the one hand there is no tissue hardening caused by "overfixing" and on the other hand the tissues do not shrink to such an extent as is usual in the case of formalin fixations.

Here, it has been found that the tissue pieces treated by means of the invention can be processed comparatively to, and sometimes even more easily than formalin-fixed tissue samples. A further advantage of the solution according to the invention is therefore the fact that tissue samples that have been fixed using this solution demonstrate excellent cutting properties, and, with such tissues that are difficult to cut when they have been fixed using solutions containing formaldehyde (for example brain tissue), there are considerable improvements to the cutting properties.

Fewer artefacts are therefore introduced into the histological section, which enables a significant improvement of the microscopic examination of the sample and therefore considerably facilitates the diagnosis of histological anomalies and abnormalities.

As a result, the stains can be differentiated not only identically, but much more firmly and much better compared with stains on formalin-fixed samples, since colour differences in the histological section are sharper and more vibrant than is the case with formalin-fixed samples, and the colours themselves are brighter and more selective for differences in the chemism of the tissue.

The tissue preservation is additionally advantageous. Shrinkage hardly occurs, and when it does it is to a much smaller extent than with formalin fixations. Cell nuclei retain their round shape and can be stained very well using conventional nucleus dyes. Even in the finest of structures, an excellent preservation can be observed, which even equals the preservation of fixations using fixation agents containing sublimate and picric acid.

The simple handing is also advantageous. The established laboratory routines do not have to be changed, since fixing times and application can remain identical. Tissue samples are introduced into the sample containers with the invention and remain there until further processed. The fixing times correspond to those of formalin. Longer fixations are not problematic and may even be advantageous. However, an unwanted overfixing of the tissue during treatment with the solution according to the invention should not be observed in any case. Further, the declared solution is harmless in terms of hazardous materials and dangerous substances and can also be handled as harmless chemical waste with regard to disposal.

The invention furthermore also relates to the use of the solution as a preservative for macroscopic preparations, that is to say including entire animal bodies or corpses, as are used in the field of anatomical science. In addition, it can also be used for the fixing and long-term preservation of biological sample material in natural history museums, zoological or botanical collections, research collections and teaching collections.

The invention also relates to the use of the fixation agent for immunohistochemical stains with paraffin-conventional antibodies and also for antibodies that are suitable for frozen sections or for plastic preparations.

DETAILED DESCRIPTION OF THE PRESENTLY PREFERRED EMBODIMENTS

Examples

Example 1

Composition and Component of a Fixation Agent

| POS. | PRODUCT | % | G/L | Use Range |
|---|---|---|---|---|
| 1 | Urotropine | 4 | 40 | up to 20% |
| 2 | Citric acid | 5.43 | 54.29 | up to 35% |
| 3 | TWEEN 80 | 1.43 × 10E−2 | 0.143 | up to 5% |
| 4 | Monopropylene glycol | 2.86 | 28.57 | up to 20% |
| 5 | (2 E)-3-phenylprop-2-enal | 4.29 × 10E−2 | 0.429 | up to 5% |
| 6 | SPAN 80 | 0.71 × 10E−2 | 0.07 | up to 5% |
| 7 | $H_20$ or suitable solvent. | 87.65 | 876.5 | filling to 100% |
| 8 | TOTAL | | 1000 | |

Example 1.1

Calculation of the Molar Ratios of the Fixation Agent to Tissue Fixation

With a composition according to Example 1 with the components urotropine and citric acid, the molar ratio is calculated as follows:

Urotropine releases up to 6 mol formaldehyde from 1 mol urotropine. Citric acid releases up to 3 mol protons from 1 mol citric acid. 1 mol citric acid (anhydrous)=192.124 g/mol=>192.124 g; furthermore, 1 mol urotropine=140.19 g/mol=>140.19 g.

A solution that contains 4% urotropine and 5.5% citric acid (as proposed in Example 1) thus achieves a molar concentration of urotropine of 0.28 M and can form at most up to 1.71 M formaldehyde. Further, the molar concentration of citric acid is 0.28 M and can form at most up to 0.85 M protons.

This means that, in the solution from Example 1, 0.85 mol formaldehyde can be formed from HMTA and an excess of HMTA also remains in the solution. The molar ratio between total releasable aldehyde and total protons releasable from the acid is in this case approximately 2:1, wherein it must be taken into consideration that urotropine is present in excess.

Figure 1:
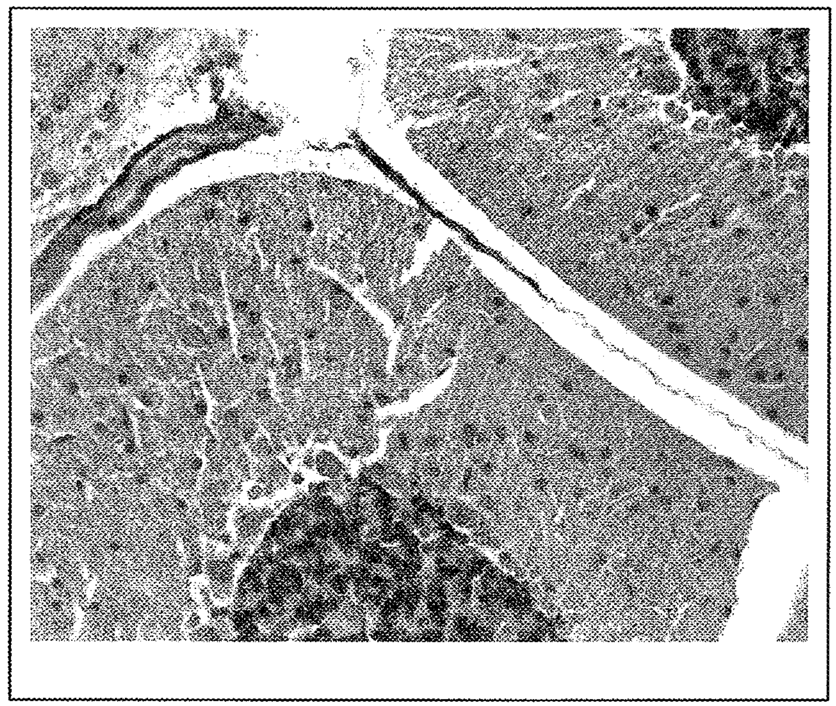
FIG. 1: shows a comparison of staining results of an AZAN stain on a tissue sample, specifically rat cerebellum, wherein the sample used for FIG. 1A was fixed using formalin 4% in accordance with standard methods and the sample used for FIG. 1B was fixed in an identical method, but using the solution according to the invention. It can be clearly seen that FIG. 1B has fewer cracks, demonstrates an improved preservation of the preparation and of the neurons, and also adopts a more vibrant staining.
Figure 1:
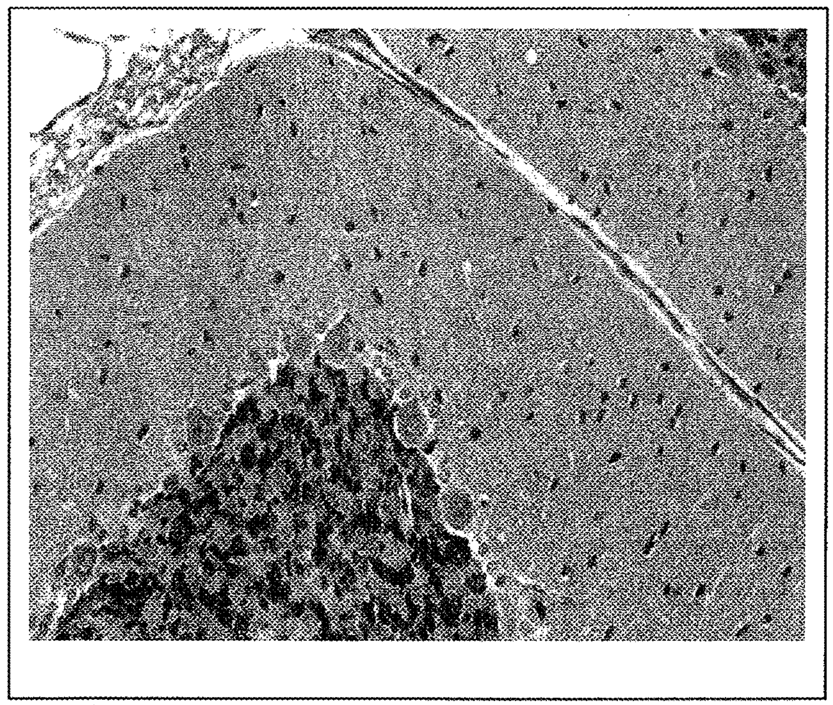
Figures 2A, 2B:
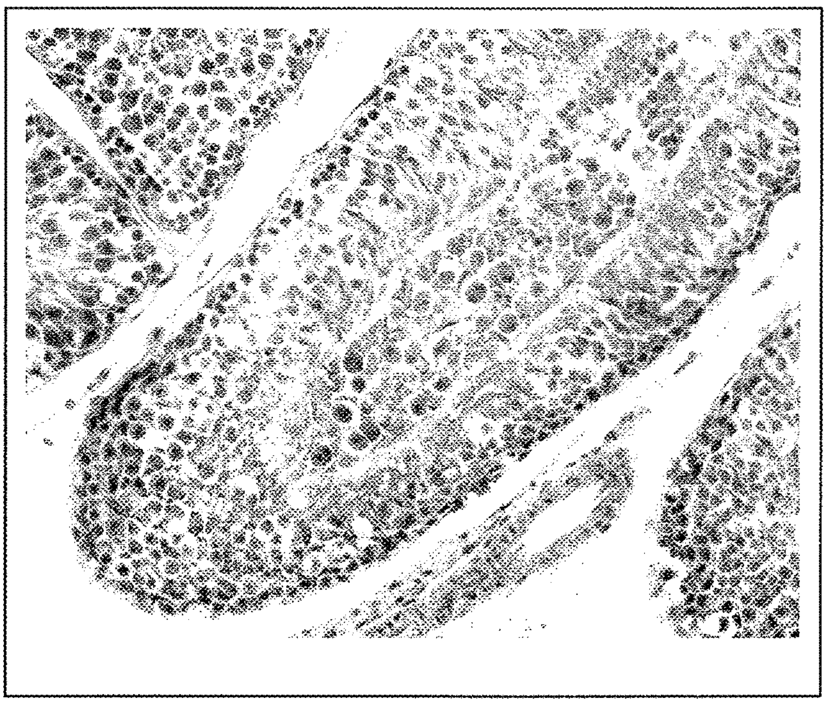
FIG. 2: shows a comparison of staining results of a HAEMOTOXYLIN & EOSIN (H&E) stain on a tissue sample, specifically rat testes, wherein the sample used for FIG. 2A was fixed using formalin 4% in accordance with standard methods and the sample used for FIG. 2B was fixed in an identical method, but using the solution according to the invention. It can be clearly seen that FIG. 2B has clear delimited structures, fine structures are better preserved, and the sample adopts a more vibrant staining.
Figure 3:
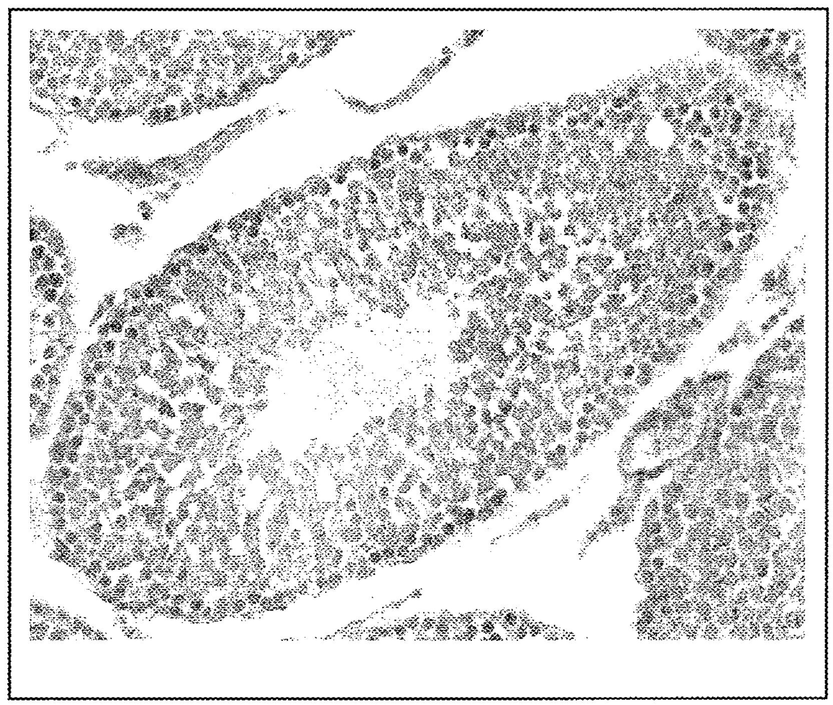
FIG. 3: shows a comparison of staining results of an MSB LENDRUM stain on a tissue sample, specifically rat testes, wherein the sample used for FIG. 3A was fixed using formalin 4% in accordance with standard methods and the sample used for FIG. 3B was fixed in an identical method, but using the solution according to the invention. It can be clearly seen that in FIG. 3B the differentiation of the fine structures is better, and the sample adopts a more vibrant staining.
Figure 3:
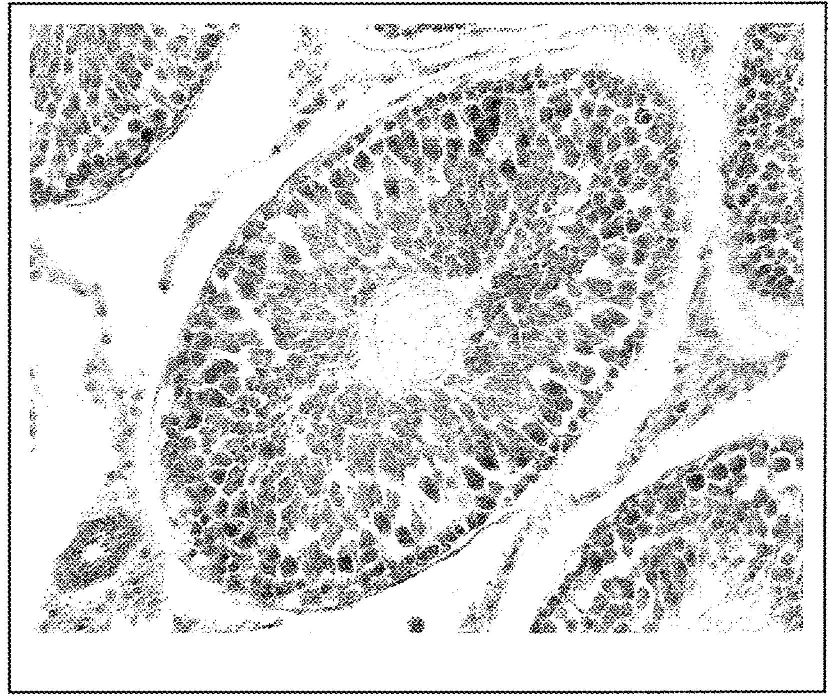
Figure 4:
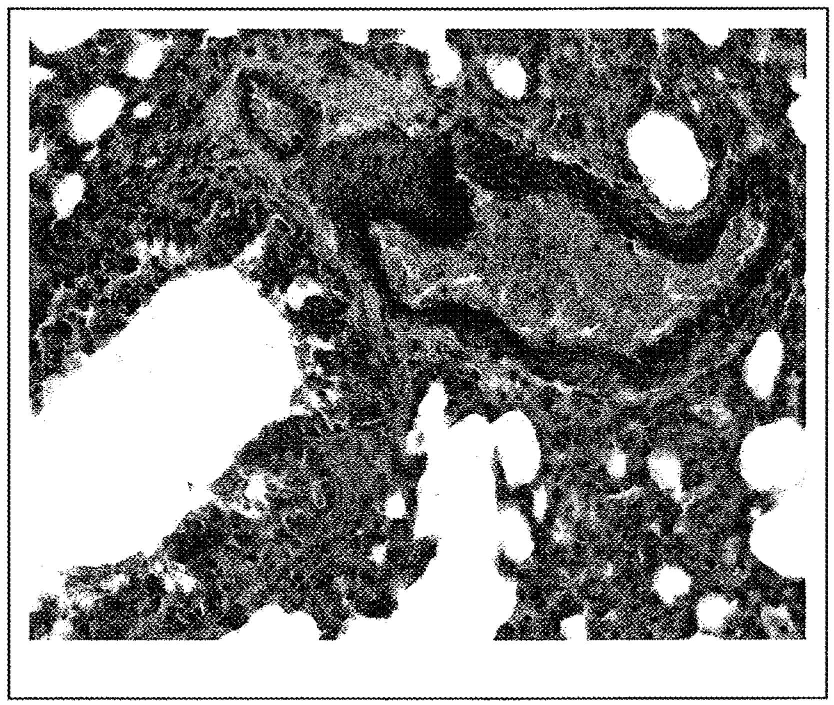
FIG. 4: shows a comparison of staining results of a MOVAT stain on a tissue sample, specifically rat lung, wherein the sample used for FIG. 4A was fixed using 4% formalin in accordance with standard methods and the sample used for FIG. 4B was fixed in an identical method, but using the solution according to the invention. It can be clearly seen that FIG. 4B has clearer delimited structures, fine structures (bronchi and alveoli) are better preserved, and the sample adopts a more vibrant staining.
Figure 4:
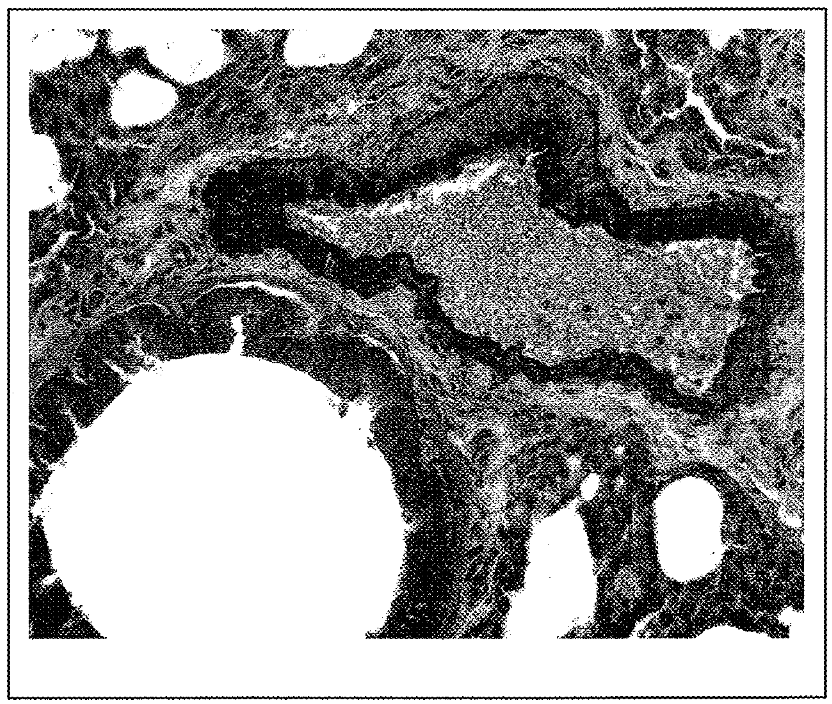
Figure 5:
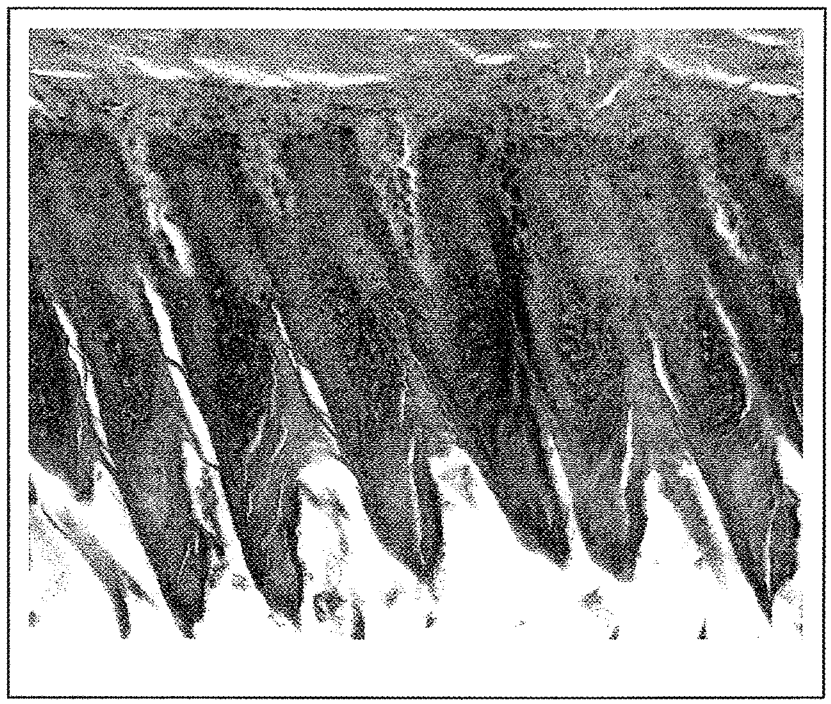
FIG. 5: shows a comparison of staining results of a MASSON TRICHROME stain on a tissue sample, specifically rat tongue, wherein the sample used for FIG. 5A was fixed using formalin 4% in accordance with standard methods and the sample used for FIG. 5B was fixed in an identical method, but using the solution according to the invention. It can be clearly seen that FIG. 5B has a sharper differentiation of the fine structures, the stain leads to cell nuclei stained more vibrantly, and the sample as a whole adopts a more vibrant staining.
Figure 5:
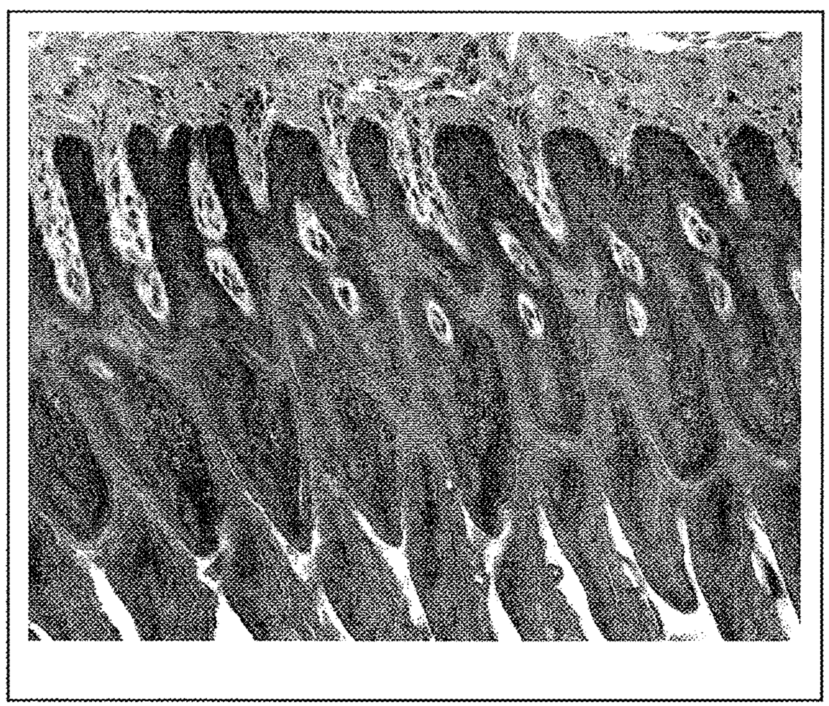

In the case of a balanced reaction, in which 0.85 mol formaldehyde can be formed, the solution functions excellently as a fixation solution for histology (see Example 5 and FIGS. 1 to 5).

1.2. Comparative Calculation

On the Example of Another Conventional Solution

A known solution containing 1% hexamethylenetetramine (HMTA) and 1% citric acid, in accordance with the corresponding calculation as under Example 1.1, has a molar concentration of HMTA of 0.07 M and can form at most up to 0.42 M formaldehyde. Here, the molar concentration of citric acid is 0.052 M and can form at most up to 0.156 M protons.

This means that, with this known solution, at most 0.156 mol formaldehyde can be formed from HMTA and an excess of HMTA remains in the solution. The molar ratio between total releasable aldehyde and total protons releasable from the acid is in this case approximately 2.6:1.

If a maximum of 0.156 mol formaldehyde is formed, the solution does NOT function as a fixation solution for histology, since all known side-effects occur, as also described in the text above, such as shrinkage and morphological changes up to the onset of degeneration of the tissue. The aforementioned values were confirmed by way of experiment for HMTA and citric acid.

Example 2

Composition and Components of a Further Preferred Embodiment

| PRODUCT | % | G/L | Use Range |
|---|---|---|---|
| Hexamethylol melamine | 6 | 60 | 0-20% |
| Boric acid | 3 | 30 | 0-35% |
| Sodium hydroxide | 0.4 | 4 | 0-5% |
| Dipropylene glycol | 2.86 | 28.57 | 0-20% |
| Phenylmethanal | 0.01 | 0.1 | 0-5% |
| Polysorbate 20 | 0.01 | 0.1 | 0-5% |
| $H_20$ or suitable solvent | 87.65 | 876.5 | 10-99% |
| TOTAL | | 1000 | |

Hexamethylol melamine, referred to hereinafter as HMM, enters into the following balanced reaction:

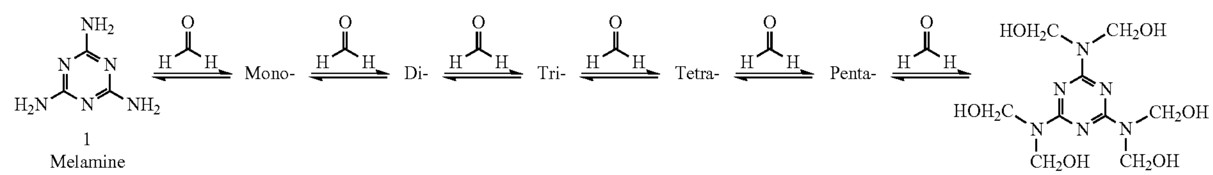

HMM

This reaction best takes place at pH 6-8, which is why a weak acid, specifically boric acid, is used in accordance with the present embodiment. The pH is adapted with sodium hydroxide. It may be that –>6 mol formaldehyde are released per mol HMM. This gives:

| | |
|---|---|
| 1 mol HMM | 270 g |
| 1 mol formaldehyde | 30 g |
| 1 mol HMM contains 6 mol aldehyde or | 180 g |

In order to obtain a solution with total releasable formaldehyde content of 4%/l, 40 g releasable formaldehyde or 60 g HMM are consequently required.

Three protons are cleaved from the boric acid. Boric acid can be represented by the formula $H_3BO_3$ and has a molar mass of 61.83 g. In order to obtain 6 mol of protons, 27.5 g are therefore required, that is to say 30 g of boric acid calculated with slight excess, based on 1000 ml solution.

In the present composition, a ratio of total releasable aldehyde/total releasable protons of approximately 1:1 is produced.

Example 3

Further Alternative Embodiments

In accordance with the calculations presented above in Example 1.1 and also Example 2, further alternative compositions can be prepared. The components that can be used alternatively are specified in the table below.

Any combination of the substances specified under Position 1 with the substances from Position 2 is possible. Where appropriate, the substances from Position 5 are combined, for example in order to thus adjust the proportion of total releasable aldehyde. In accordance with the invention, a solution formed by these combinations must comprise at least 0.5 mol/l of total releasable aldehyde. The substance alternatives of Positions 3 and 4 and also 6 and 7 are optional and can be combined as necessary.

| POSITION based on the table in Example 1 | ALTERNATIVE COMPONENTS |
|---|---|
| 1 | urotropine, triazines, dimethylol, dihydroxyethylene urea, tetramethylol acetylene diurea, mono-, di-, tri-, tetra-, penta- or hexamethylol melamine, dimethyl propylene urea, acetoguanamine or 5,5-dimethyl-hydantoin, or mixtures thereof |
| 2 | oxalic acid, tartaric acid, succinic acid, hydrochloric acid, acetic acid, propionic acid, formic acid, mono-, di- or trichloroacetic acid or chloroacetic acid, uric acid, citric acid, boric acid, phosphoric acid, or mixtures thereof |
| 3 | TWEEN 80, polysorbate 20, 40, 60 or 80, alkalines, lauryl sulfates; dodecyl sulfates, dodecyl sulfonates, dodecylbenzene sulfonates; ethoxylated fatty acids; ionic and non-ionic surfactants with high HLB (hydrophilic-lipophilic balance) value, (in chemistry describes the hydrophilic and lipophilic proportion of primarily non-ionic surfactants and was proposed in 1954 by W. C. Griffin. Surfactants with a high HLB value cause a good wetting of hydrophilic surfaces), or mixtures thereof |
| 4 | mono-, di- or further polypropylene glycols; glycerol, mono-, di-, or further polyethylene glycols; sorbitol, pentaerythritol, low-molecular PEG, high-molecular PEG, and mixtures thereof |
| 5 | citral, 3,7-dimethylocta-2,6-dienal, geranial, (E)-3,7-dimethylocta-2,6-dienal, propanal, butanal, valeric aldehyde, pentanal, hexanal, heptanal, octanal, nonanal, decanal, (2 E)-3-phenylprop-2-enal, benzaldehyde, phenylmethanal, vanillin aldehyde, 4-hydroxy-3-methoxyphenyl-methanal, and mixtures thereof |
| 6 | SPAWN 80, polysorbates, lauryl sulphates, ethoxylated fatty acids, ionic and non-ionic surfactants with low HLB, or mixtures thereof |
| 7 | $H_2O$; alcohols; acetones; dimethyl sulfoxide; alkyl carbonates; polar organic solvents, and mixtures thereof |

Example 4

Method for the Preparation of Histological Samples for Microscopic Examination In accordance with the inventive method, the tissue sample should be introduced as fresh as possible into the fixation solution, for example the solution according to Example 1. Generally, it is usual for the quantity of fixation solution to correspond to twenty times the sample volume and for the fixation period to be dependent on the sample size. Depending on size, the samples remain in the fixation solution from 12 to 36 hours, and larger samples may also remain in the fixation solution for 72 hours or longer. A diffusion distance or penetration rate of 1 mm in 2-4 hours is assumed.

In order to then embed the sample in paraffin or other embedding agents, a complete dewatering of the sample is necessary. The sample is first removed from the fixation solution, washed in flowing water and immersed in a series of alcohols in rising concentration. The steps between the concentration stages are here 30-50-60-70-80-90-96-100, for example. Ethanol or isopropanol are usually used as alcohols. Following the dewatering, the sample is immersed in a suitable organic solvent, which is miscible both with alcohol and with the embedding medium, then the infiltration with the actual embedding medium (paraffin) follows in a number of stages, in each case for a number of hours (depending on the sample size). The sample is cast into a suitable mould with a small quantity of paraffin. Once the block has solidified, the block is removed from the mould and then can be cut. Using a suitable microtome, sections 4-6 μm thick are produced and are arranged on glass slides.

The glass slides with the paraffin sections can be stored for a relatively long period of time. However, further processing, that is to say staining, generally occurs directly. Here, the paraffin first has to removed again and the tissue section itself watered. The procedure previously described is performed in the reverse order, that is to say the paraffin is dissolved out using xylene, followed by alcohol 96%, 90%, 80%, 70% or a similar sequence up to water. The staining then starts, wherein, in the case of dyes that are present in alcohol solution, the steps up to complete watering can be omitted and the glass slides can be immersed directly into the alcohol staining solution.

Example 5

Assessment of the Morphological Preservation, Cuttability and Stainability of Paraffin Preparations With the aid of conventional histological stains, it was possible to carry out a diagnostic evaluation of section samples. The sections were produced from tissues which had previously been fixed either in the solution from Example 1 or in 4% formalin. The qualitative evaluation was performed on four stains selected by way of example: (1) haematoxylin & eosin (HE), (2) Azan according to Geidies, (3) Masson Goldner Trichrome and (4) MSB Lendrum. The histological diagnostic evaluation detects the parameters morphological preservation and stainability of the sections. The parameter cuttability was assessed during the cutting process performed on various tissues.

Stains Used by Way of Example

HAEMOTOXYLIN & EOSIN: the conventional H & E stain uses the dyes haematoxylin in the composition according to Mayer and eosin. Both dyes are offered in aqueous solution (eosin possibly also as alcohol solution) with a defined pH value and/or a defined acid addition and provide a characteristic colour image. Cell nuclei are generally stained blue-purple here. In this case, the dye haematoxylin, which is offered as Alaun complex, reacts with the chromatin of the cell nuclei. In order to obtain a stable water- and alcohol-insoluble coating, this compound is then immersed in tap water or in a salt solution mixed with monovalent metal ions. The eosin solution is set in aqueous form to a pH value of approximately 4.0, which leads to a characteristically illuminating orange colour image. Eosin binds in different intensity to various tissue and cell structures and thus allows a good differentiation of the histological section.

MASSON GOLDNER TRICHROME: the Masson Goldner Trichrome and the Crossman stain are also conventional histological stains which function as Trichrome staining with three (or four) dyes. Here too, the nuclei are stained with haematoxylin, but not with an Alaun complex, but via an iron complex. This does not lead to a cell nucleus stained blue-purple, but to a brown-black cell nucleus, which can be differentiated very clearly, even with respect to tissue components stained blue. A mixture of acid fuchsin, ponceau and azophloxine is used as a second dye and binds differently to different tissue regions and makes it possible to identify cell plasma and other intracellular structures. This dye complex reacts directly with the respective tissue structures. A further dye, Orange G, is what is known as a mordant dye, which forms a water- and alcohol-insoluble coating with certain tissue structures only in the presence of a bivalent metal ion, for example as is provided by phosphotungstic acid or phosphomolybdic acid. In particular, erythrocytes and muscles can be presented using this dye and can be significantly distinguished from other tissues. Keratinous material is also stained considerably with Orange G. Alternatively, aniline blue or light green is used as a fourth dye. These are conventional fibre dyes, which bind particularly with collagens and intercellular structures. Cartilage and bone material also bind to these dyes, depending on chemism. Different blue or green intensities ultimately allow diagnostic conclusions concerning the fibre composition, wherein aniline blue generally provides the differentiated image.

MSB LENDRUM: the MSB Lendrum stain is a stain related to the Masson Goldner Trichrome, in which, however, the dyes Martius yellow and crystal ponceau are offered instead of acid fuchsin/azophloxine/ponceau and instead of Orange G. This results in an image that is comparable, but differentiated further still, wherein the significance of the MSB staining is of particular value, especially for vascular structures, because muscles, fibre arrangement and vessel inner walls are better differentiated here than with the previously mentioned Trichrome stains.

AZAN ACCORDING TO GEIDIES: the AZAN stain also belongs to the series of conventional Trichrome staining. The original variant according to Heidenhain works in the pre-treatment of the sections with aniline alcohol, azocarmine for nucleus staining, phosphotungstic acid for staining and a dye mixture of aniline blue and Orange G and lasts for a number of hours. By contrast, the variant modified according to Geidies dispenses with aniline alcohol, and instead uses the azocarmine nuclear fast red and drastically reduces the staining times. The result of the stain is so similar that the conventional AZAN stain can be largely replaced. The results are substantially comparable to those of the Masson Goldner and MSB Lendrum. Cell nuclei are stained deeply red by the nuclear fast red provided in aluminium sulfate solution and contrast well with the continuous blue background. Aniline blue and Orange G produce the counter or background stain (blue) and a well differentiated staining of the erythrocytes (orange) and of the muscle plasma (also deeply orange). In addition, creatine and callous epithelia are also stained significantly orange. The basic substance and fibres obtain different blue shades as a result of the aniline blue. The result of the aniline blue stain is influenced on the whole very strongly by the stain duration.

5.1 Morphological Preservation

In order to assess the morphological preservation at light microscopy level, the following parameters can be used: (A) fragmentation of the tissue (crack formations) and (B) the presentation of the cell nuclei (nuclei) and (C) of the cell bodies (stomata).

The fragmentation of the tissue by the formation of individual cracks or propagated crack networks results from deficient fixing and manifests itself as the tissue section is drawn on the hot water bath or the hot plate and also during the staining process. During the course of the heat-induced drawing of the paraffin and therefore also of the tissue section penetrated and covered by paraffin, a physical loading of the paraffin/tissue association is produced, which may result, in the case of deficient fixing, in the breaking of the tissue. The tensile and/or shear forces occurring during deparaffinisation and staining of the tissue section are applied particularly to these tissue points, which are already strained during the drawing process, expand these tissue points or break the tissue entirely. The tendency for crack formation is proportional to the adhesive property of the slide used.

The score is awarded between (no fragmentation of the tissue, 1) and (cell nuclei and cell bodies in their natural form, 1) and (tissues destroyed by crack formation and detached, 4) and (cell nuclei angular and severely shrunken, cell body massively shrunken with strong "ring formation", 4).

General Criteria

| Fragmentation | Score | Cell nuclei | Score | Cell body | Score |
|---|---|---|---|---|---|
| No fragmentation | 1 | Natural | 1 | Natural | 1 |
| Slight fragmentation | 2 | Slightly angular | 2 | Minimal shrinkage | 2 |
| Moderate fragmentation | 3 | Moderately angular | 3 | Moderate shrinkage | 3 |
| Extreme fragmentation: tissue is destroyed over a large area | 4 | Cell nucleus angular and severely shrunken | 4 | Massive shrinkage and/or ring formation | 4 |

5.2 Cuttability

A further criterion in the histological processing of tissue samples is what is known as the cuttability of the tissue. The different properties of fixation agents result, usually in accordance with the incubation time, in a different cuttability or load-bearing capacity of the tissue. A tissue, for example, can be brittle and fragile (no cuttability, 4) or supple and resistant (high cuttability, 1) as a result of the fixation. Different tissue properties of different tissue types have to be taken into consideration in the assessment.

General Criteria

| Cuttability | Score |
|---|---|
| High cuttability | 1 |
| Above-average cuttability | 2 |
| Below-average cuttability | 3 |
| No cuttability | 4 |

5.3 Stainability

Histological stains of tissue sections often allow various distinctions between individual cells, but also tissue types, depending on the dye combinations used. This histological differential diagnosis applied in human and veterinary diagnostics, but also in medical, zoological and botanical research, is based on the differentiation of nucleus types, but in particular also on the differentiation of dye precipitation on cells and/or tissues. A maximum dye saturation, uniform colour precipitation, good contrasting (between cell nucleus and cell body) and also a high colour brilliance are therefore not only desirable, but also absolutely necessary requirements of a stain.

Chemical reactions between the fixation agent and the tissue influence not only the cuttability and the load-bearing capacity of the tissue, but also the stainability thereof. Different fixation agents can improve, but also reduce the stainability of a tissue section depending on the incubation time. In order to determine the stainability of tissues, the following criteria are used: 1. colour saturation, 2. uniform colour precipitation, 3. contrast between cell nucleus and cell body and 4. colour brilliance. The individual stains have to be assessed separately from one another, since stains or components thereof respond differently to the influence of fixation agents.

General Criteria

| 1. Colour saturation | Score |
|---|---|
| Very good colour saturation | 1 |
| Good colour saturation | 2 |
| Moderate colour saturation | 3 |
| Inadequate colour saturation | 4 |

| 2. Colour precipitation | Score |
|---|---|
| Uniform colour precipitation without oversaturation | 1 |
| Colour precipitation with low fluctuations | 2 |
| Partly irregular colour precipitation | 3 |
| Completely irregular colour precipitation | 4 |

| 3. Contrast (cell nucleus/cell body) | Score |
|---|---|
| Very good contrast (generally good differentiability of nucleus components and/or nucleus membranes) | 1 |
| Good contrast (largely good differentiability of nucleus components and/or nucleus membranes) | 2 |
| Moderate contrast (little differentiability of nucleus components and/or nucleus membranes) | 3 |
| Poor contrast (no differentiability of nucleus components and/or nucleus membranes) | 4 |

| 4. Colour brilliance | Score |
|---|---|
| Very high colour brilliance | 1 |
| High colour brilliance | 2 |
| Low colour brilliance | 3 |
| Very low colour brilliance | 4 |

5.4 Evaluation/Result

The described criteria catalogue forms the basis for the presentation below of the results in table form. Section samples were produced following a 24/hr fixation period in the solution according to Example 1 or 4% formalin from the following tissues: brain, heart, lung, kidney, skin and testes. These were then stained simultaneously with HE, Azan according to Geidies, Masson Goldner Trichrome and MSB Lendrum.

1. Morphological preservation:

| Criterion | Solution according to Example 1 | Formalin |
|---|---|---|
| Fragmentation | 1 | 3 |
| Cell nuclei | 2 | 2 |
| Cell bodies | 2 | 2 |

2. Cuttability

| Tissue type | Solution according to Example 1 | Formalin |
|---|---|---|
| Brain | 1 | 2 |
| Heart | 2 | 2 |
| Lung | 2 | 3 |
| Kidney | 2 | 3 |
| Skin | 1 | 2 |
| Testes | 1 | 2 |

3.a. Stainability (H & E):

| Criterion | Solution according to Example 1 | Formalin |
|---|---|---|
| 1. Colour saturation | 1 | 2 |
| 2. Colour precipitation | 2 | 3 |
| 3. Contrast | 1 | 2 |
| 4. Colour brilliance | 1 | 2 |

| 3.b. Stainability (Azan according to Geidies) | | |
|---|---|---|
| Criteria | Solution according to Example 1 | Formalin |
| 1. Colour saturation | 1 | 2 |
| 2. Colour precipitation | 2 | 2 |
| 3. Contrast | 2 | 2 |
| 4. Colour brilliance | 1 | 3 |

| 3.c. Stainability (Masson Goldner Trichrome): | | |
|---|---|---|
| Criteria | Solution according to Example 1 | Formalin |
| 1. Colour saturation | 1 | 2 |
| 2. Colour precipitation | 2 | 3 |
| 3. Contrast | 1 | 2 |
| 4. Colour brilliance | 1 | 3 |

| 3.d. Stainability (MSB Lendrum): | | |
|---|---|---|
| Criteria | Solution according to Example 1 | Formalin |
| 1. Colour saturation | 1 | 3 |
| 2. Colour precipitation | 2 | 3 |
| 3. Contrast | 2 | 4 |
| 4. Colour brilliance | 2 | 4 |

The invention claimed is:

1. A fixation agent for tissue samples, comprising:

at least one polyamine, selected from the group consisting of urotropine, dimethylol dihydroxyethylene urea, mono-, di-, tri-, tetra-, penta- or hexamethylol melamine, tetramethylol acetylene diurea, dimethylol propylene urea, acetoguanamine or 5,5-dimethylhydantoin, and mixtures thereof, and at least one acidification agent selected from the group of free monovalent, bivalent or polyvalent acid consisting of oxalic acid, fumaric acid, tartaric acid, maleic acid, succinic acid, hydrochloric acid, acetic acid, propionic acid, formic acid, mono-, di- or tri chloroacetic acid or chloroacetic acid, boric acid, phosphoric acid, citric acid, and mixtures thereof, wherein the polyamine reacts with protons released from the acidification agent, thus forming or releasing aldehydes, and the molar ratio between the molar concentration of releasable aldehyde per mol of amine to the molar concentration of releasable protons per mol of acid lies in a range from 1:0.7 to 1:1.5.

2. The fixation agent according to claim 1, further including at least one further polyfunctional aldehyde selected from the group consisting of citral, 3,7-dimethylocta-2,6-dienal, geranial, (E)-3,7-dimethylocta-2,6-dienal, propanal, butanal, valeric aldehyde, pentanal, hexanal, heptanal, octanal, nonanal, decanal, (2 E)-3-phenylprop-2-enal, benzaldehyde, phenylmethanal, vanillin aldehyde, 4-hydroxy-3-methoxyphenylmethanal, and mixtures thereof.

3. The fixation agent according to claim 1, wherein the molar concentration of the total available aldehyde in the solution is at least 0.5 mol/1.

4. The fixation agent according to claim 1, wherein it is present in aqueous solution.

5. The fixation agent according to claim 1, wherein it is set to a pH range of 3-8.

6. The fixation agent according to claim 1, further including at least one strongly hydrophilic compound selected from the group consisting of monopropylene glycol, dipropylene glycol, polypropylene glycol, glycerol, pentaerythritol, sorbitol, ethylene glycol, diethylene glycol and polyethylene glycol.

7. The fixation agent according to claim 1, further including at least one surfactant selected from the group consisting of ethoxylated non-ionic surfactants with high and/or low HLB value, polysorbates, particularly polysorbate 20, 40, 60 or 80, saponins, alkali salts of decyl sulfates, decyl sulfonates, dodecyl sulfates, dodecyl sulfonates and dodecylbezenesulfonates, oleates, stearates, caprates, caprylates and betaines.

8. The fixation agent according to claim 1, wherein it is present as anhydrous mixture of crystalline or anhydrous components, which are added in the form of soluble powder or as soluble pressed tablets to a suitable solvent.

9. A method for staining tissue samples fixed in a formalin-free manner, comprising:

in a first step the tissue sample is fixed with the fixation agent according to claim 1, in a second step the tissue sample is prepared for staining, in a third step the tissue sample is stained, and is evaluated microscopically.

10. Use of the fixation agent according to claim 1, for preparing and fixing tissues samples for histological or immunohistochemical stains of the tissue sample.

11. The method of claim 9 wherein the second step includes cutting the tissue sample.

12. The use of the fixation agent according to claim 10 without utilizing formalin.

13. The fixation agent according to claim 1, wherein the at least one polyamine includes urotropine and the at least one acidification agent includes citric acid.

14. The fixation agent of claim 13, wherein the fixation agent includes up to twenty percent by mass of urotropine and up to thirty five percent by mass of citric acid.

15. The fixation agent of claim 13, wherein the fixation agent includes four percent (4%) by mass of urotropine and five point forty three percent (5.43%) by mass of citric acid.

16. The fixation agent of claim 15, further including: one point four three times 10E-2 percent (1.43×10E-2%) by mass of TWEEN 80; two point eight six percent (2.86%) by mass of mono propylene glycol; and four point twenty nine times 10E-2 percent (4.29×10E-2%) by mass of (2E)-3-Pheylprop-2-enal.

17. The fixation agent of claim 16, further including: zero point seventy one times 10E-2 percent (0.71×10E-2%) by mass of SPAN 80; and eighty seven point fourteen percent (87.14%) water.

* * * * *